United States Patent
Curcio et al.

(10) Patent No.: US 6,638,302 B1
(45) Date of Patent: *Oct. 28, 2003

(54) STENT FOR ANGIOPLASTY AND ASSOCIATED PRODUCTION PROCESS

(75) Inventors: Maria Curcio, Saluggia (IT); Giovanni Rolando, Chivasso (IT); Franco Vallana, Turin (IT)

(73) Assignee: Sorin Biomedica Cardio S.p.A., Saluggia (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/997,597

(22) Filed: Dec. 23, 1997

(30) Foreign Application Priority Data

Dec. 30, 1996 (IT) .......................... TO96A1095

(51) Int. Cl.[7] .................................. A61F 2/06
(52) U.S. Cl. .................. 623/1.46; 623/1.44; 427/2.1
(58) Field of Search ................ 623/1, 12, 1.15, 623/1.22, 1.37–1.48; 606/151; 600/37; 427/2.1–2.31; 424/423–426

(56) References Cited

U.S. PATENT DOCUMENTS 3,700,380 A * 10/1972 Kitrilakis ................... 623/1.15
4,219,520 A * 8/1980 Kline .............................. 623/1

(List continued on next page.)

FOREIGN PATENT DOCUMENTS

| EP | 0 274 846 A1 | 7/1987 |
| EP | 0 540 290 A2 | 10/1992 |
| EP | 0 601 804 A1 | 6/1994 |
| EP | 0 603 959 A1 | 6/1994 |
| EP | 0 701 803 A1 | 3/1996 |
| EP | 0 747 069 A2 | 11/1996 |
| EP | 0 875 218 A2 | 11/1998 |
| WO | WO 95/09659 A1 | 4/1995 |
| WO | WO 95/12369 | 11/1995 |
| WO | WO 96/03092 A1 | 2/1996 |
| WO | WO 96/12450 A | 5/1996 |
| WO | WO 98/34669 | 8/1998 |
| WO | WO 98/56312 | 12/1998 |
| WO | WO 00/12147 | 9/2000 |
| WO | WO 00/76557 A1 | 12/2000 |

OTHER PUBLICATIONS

De Schreerder et al., "Local Angiopeptin Delivery Using Coated Stents Reduces Neointimal Proliferation in Overstretched Porcine Coronary Arteries," *J. Invas. Cardiol.*, 8:215–222 (1996).

Guzman et al., "Local Intraluminal Infusion of Biodegradable Polymeric Nanoparticles," *Circulation*, 94:1441–1448 (1996).

Labinaz et al., "Biodegradable Stents: The Future of Interventional Cardiology?" *Journal of Interventional Cardiology*, 8(4):395–405 (1995).

Stack, "Local Drug Delivery: The Development of a Drug Delivery Stent," *The Journal of Invasive Cardiology*, 8(8):396–397 (Oct. 1996).

Topol, *Textbook of Interventional Cardiology*, 2(2):687–815 (1994).

*Primary Examiner*—David H. Willse
*Assistant Examiner*—Suzette J. Jackson
(74) *Attorney, Agent, or Firm*—Popovich & Wiles, P.A.

(57) ABSTRACT

The stent (1) has surface sculpturing, preferably on its outer surface (2) only, constituted, for example, by microspheres (3), having the function of increasing the actual geometric surface area of the stent, of creating undercuts and roughness to encourage the application of coatings of active or activatable agents, as well as of improving the attachment of the stent (1) to the blood vessel wall.

7 Claims, 1 Drawing Sheet

U.S. PATENT DOCUMENTS

| | | | | |
|---|---|---|---|---|
| 4,254,180 A | * | 3/1981 | Kline | 623/1 |
| 4,503,569 A | | 3/1985 | Dotter | |
| 4,729,766 A | * | 3/1988 | Bergen et al. | 623/1 |
| 4,767,418 A | * | 8/1988 | Deininger et al. | 623/1.15 |
| 4,768,507 A | | 9/1988 | Fischell et al. | |
| 4,776,337 A | | 10/1988 | Palmaz | |
| 4,800,882 A | | 1/1989 | Gianturco | |
| 4,830,003 A | | 5/1989 | Wolff et al. | |
| 4,856,516 A | | 8/1989 | Hillstead | |
| 4,886,062 A | | 12/1989 | Wiktor | |
| 4,907,336 A | | 3/1990 | Gianturco | |
| 4,932,964 A | * | 6/1990 | Bittmann et al. | 623/1.15 |
| 5,015,253 A | * | 5/1991 | MacGregor | 623/1.15 |
| 5,213,580 A | * | 5/1993 | Slepian et al. | 623/1.15 |
| 5,356,433 A | | 10/1994 | Rowland et al. | |
| 5,449,373 A | | 9/1995 | Pinchasik et al. | |
| 5,455,100 A | * | 10/1995 | White | 428/31 |
| 5,609,629 A | | 3/1997 | Fearnot et al. | |
| 5,643,580 A | | 7/1997 | Subramaniam | |
| 5,672,638 A | | 9/1997 | Verhoeven et al. | |
| 5,718,973 A | * | 2/1998 | Lewis et al. | 428/36.5 |
| 5,723,004 A | * | 3/1998 | Dereume et al. | 623/1 |
| 5,728,420 A | | 3/1998 | Keogh | |
| 5,735,896 A | * | 4/1998 | Amon et al. | 623/11.11 |
| 5,746,272 A | * | 5/1998 | Mastrorio et al. | 164/516 |
| 5,788,626 A | * | 8/1998 | Thompson | 600/36 |
| 5,800,510 A | * | 9/1998 | Schmitt | 623/1 |
| 5,824,048 A | | 10/1998 | Tuch | |
| 5,824,049 A | | 10/1998 | Ragheb et al. | |
| 5,836,962 A | * | 11/1998 | Gianotti | 606/91 |
| 5,837,313 A | * | 11/1998 | Ding et al. | 427/2.21 |
| 5,843,172 A | | 12/1998 | Yan | |
| 5,846,613 A | * | 12/1998 | Neuville | 427/575 |
| 5,848,987 A | * | 12/1998 | Baudino et al. | 604/54 |
| 5,873,725 A | * | 2/1999 | Perler et al. | 433/221 |
| 5,972,027 A | | 10/1999 | Johnson | |
| 6,071,305 A | | 6/2000 | Brown et al. | |
| 6,096,070 A | | 8/2000 | Ragheb et al. | |
| 6,120,536 A | | 9/2000 | Ding et al. | |
| 6,210,436 B1 | | 4/2001 | Weadock | |
| 6,273,913 B1 | | 8/2001 | Wright et al. | |
| 6,299,604 B1 | | 10/2001 | Ragheb et al. | |

* cited by examiner

STENT FOR ANGIOPLASTY AND ASSOCIATED PRODUCTION PROCESS

FIELD OF THE INVENTION

The present invention concerns a stent for angioplasty and an associated method of production thereof.

BACKGROUND OF THE INVENTION

The term "stent for angioplasty" is intended to indicate generally devices intended for endoluminal application (for example, within a blood vessel) in association with the technique of percutaneous transluminal coronary angioplasty, or PTCA, usually effected by catheterisation of a stenotic site.

Expanding the stent at the site causes the lumen to expand giving rise to the consequent elimination of the stenosis, and the local support of the lumen by the stent, which is left in place expanded, avoids restenosis of the treated site due to the subsequent relaxation of the blood vessel wall. The use of a substantially similar structure for deploying vascular grafts and fixing them in place has already been proposed in the art: naturally, this possible extension of the field of application should be seen as included within the ambit of the present invention.

For a general review of vascular stents, reference may usefully be made to the work "Textbook of Interventional Cardiology" edited by Eric J. Topol, W. B: Saunders Company, 1994 and, in particular, to section IV of volume II, entitled "Coronary Stenting".

Many patent documents have addressed this problem, for example, U.S. Pat. No. 4,776,337, U.S. Pat. No. 4,800,882, U.S. Pat. No. 4,907,336, U.S. Pat. No. 4,886,062, U.S. Pat. No. 4,830,003, U.S. Pat. No. 4,856,516, U.S. Pat. No. 4,768,507 and U.S. Pat. No. 4,503,569.

The implantation of these devices, which is a factor in the treatment of various cardiac diseases, may require, or at least gain particular benefit from the possibility of being able to administer at the stent-implantation site agents or active principles (the two terms below in an equivalent sense) having various end purposes: they may, for example, be antithrombogenic agents or, more generally, agents for directly resisting restenosis of the treated site due to the formation of deposits, tissue proliferation, etc. In relation to this, reference may usefully be made to the following works:

"Local Drug Delivery: The Development of a Drug Delivery Stent" by Richard Stack, The Journal of Invasive Cardiology, Vol. 8, n. 8, October 1996, pp 396–397;

"Local Intraluminal Infusion of Biodegradable Polymeric Nanoparticles" by Louis A. Guzman et al., Circulation, 1996; 94; pp 1441–1448;

"Local Angiopeptin Delivery Using Coated Stents Reduces Neointimal Proliferation in Overstretched Porcine Coronary Arteries" by Ivan De Schreerder et al., the Journal of Invasive Cardiology, Vol. 8, n. 8, October 1996, pp 215–222.

Many applicational problems arise from this mode of operation, mostly related to the specific solutions adopted. For example, the problem exists of avoiding the agent or agents intended for administration in the zone of the stent being delivered or transported to different areas where they may have negative or damaging effects. Other problems may arise, for example, in ensuring the permanence and the gradual release over time of active substances capable of being, as it were, washed away by the blood passing through the stent.

These problems cannot themselves be solved or avoided by recourse to other solutions such as radioactive stents or so-called biodegradable stents, as illustrated, for example, in the work "Biodegradable Stents: The Future of Interventional Cardiology?" by M. Labinaz et al; Journal of International Cardiology, Vol. 8, n. 4, 1995, pp 395–405. Radioactive stents publicly proposed so far give rise to other problems related essentially to the fact that, in most cases, their use assumes the typical features of radiotherapy and/or nuclear medicine. The main disadvantage of biodegradable stents is that, at least in the long term when the stent has completely or substantially degraded, there is a reduction in the mechanical support of the blood vessel wall against the risk of collapse.

As a further solution for administering various kinds of active principle at the stent-implantation site a solution has recently been proposed in which at least a portion of the surface of the body of the stent (or implantation device in general) is coated with a receptor capable of binding with a ligand formed by combining an active principle with a substance capable of binding to the receptor.

In order for this new solution to be fully beneficial, that is, so that it can also be used with more conventional techniques for. effective topical administration of the active principles, it appears important to obtain a good adhesion and/or retention on the stent of the substance or substances with which these active principles are associated and/or are intended to be associated.

In relation to this it is therefore necessary to take account of various concomitant factors which often oppose one another.

In a significant number of applications it is important that the active principles are present mainly, although not exclusively, on the outer surface of the stent. Conversely, it is usually desirable that the inner surface of the stent itself is as inert as possible, that is, both from the chemical point of view and from the point of view of the possible mechanical anchorage of possible deposits.

This is the reason why currently available vascular stents are subjected to a polishing process, intended to make the surface of the stent (both inside and outside) very smooth. In relation to this, it is also possible to coat the stent with a layer of biocompatible material, such as a biocompatible carbon material (deposited, for example, using sputtering techniques), so as to confer a high degree of haemocompatability on the whole stent. Adopting this technique for the deposition of such a layer, given the very small dimensions of a stent for angioplasty, means that it is practically impossible to limit the deposition to just the inside surface of the stent. Consequently therefore, the entire surface of the stent is coated with a layer which, by its nature, makes the deposition of substances on the stent itself, in fact, impossible.

A further factor should not be forgotten: a stent for angioplasty is by its nature a heavily apertured structure, usually a mesh-like structure in which, especially in the radially-extended position, the effective surface intended to come into contact with the blood vessel wall is a small fraction of the theoretical tubular surface area defined by the outside of the stent itself In other words: even by putting the other problems described above to one side, there is very little available surface on the stent for carrying the active principles intended for local delivery.

The object of the present invention is that of resolving the disadvantages described above.

In particular, the solution according to the invention, having the characteristics referred to in the following claims, enables the selective application, specifically to the outer surface only of the stent, of a completely effective quantity of active principle (either directly or in the form of a receptor capable of binding with a ligand carrying the active principle) without by this losing the possibility of having a very smooth surface, at least inside the stent, even if clad with coatings such as haemocompatible carbon coatings.

DETAILED DESCRIPTION OF THE INVENTION

Figure 1:
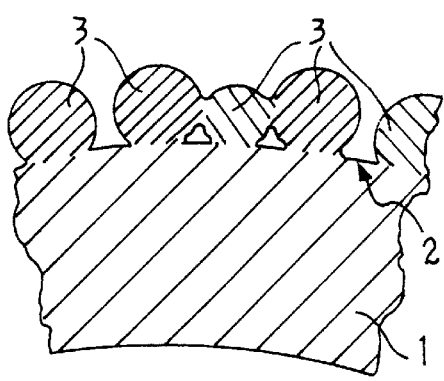
FIGS. 1 to 6 are partial enlarged views of a segment of a stent in transverse section secondary to various embodiments of the invention.

The invention, which concerns a stent as well as the associated procedure for the manufacture thereof, will now be described with reference to the accompanying drawings, comprising FIGS. 1 to 6, which illustrate different possible embodiments of the invention.

In all of the accompanying Figures, the reference numeral 1 indicates a wall portion of a stent for angioplasty. By way of example, FIGS. 1 to 6 can be considered as partial views on an enlarged scale of a segment of a stent in transverse section. Such a section is usually circular in shape regardless of whether the stent is radially-contracted or radially-expanded.

The specific details of construction of the stent and, in particular, its geometry, are factors which are in themselves clear in the context of the invention and which apply regardless of the particular structure of the stent. This is also substantially true as regards the basic manufacturing technique (for example, starting from a wire or microtube which is then subjected to an operation for cutting the apertures, for example, using lasers) and/or the material (usually metal) of which the stent is made. All of these factors are dealt with in a fairly large volume of literature and do not require detailed description here.

In essence, the invention provides for the formation of surface sculpturing on the stent 1, at least—and preferably—over a part of, or the whole of the outer surface, indicated 2, and having substantially the aim of:

increasing the theoretical surface area of the stent in order to encourage the application of coatings, such as those intended to carry or bind active principles, creating in any case undercuts and roughness so as to form anchorage sites for the substances, without requiring specific surface-adhesion sites, and, as a complementary advantage, improving the attachment of the stent to the blood vessel wall that is already in the acute phase, specifically by preventing relative movements which can give rise to microlesions.

For clarity, the term "sculpturing" is used to distinguish clearly the surface conformation attributed to the stent according to the invention from the degree of surface (residual) roughness that the surfaces of the stent have in any case, even when they have been previously subjected, according to convention, to a polishing or finishing process.

By way of example, one such treatment confers such a degree of residual roughness on the stent surfaces that the peak-to-trough distances recognisable in a theoretical section of the surface in question at right angles to the surface itself are not, in any case, greater than approximately 2–3 microns.

The degree of surface irregularity, or sculpturing, characteristic of the invention is, instead, such that the peak-to-trough distances found in similar conditions are, typically approximately 10–20 microns, that is, with the possibility of achieving values of an order of magnitude even greater than those of the normal surface finishing of a stent.

FIGS. 1 to 6 illustrate, in order of current preference, different techniques that can be used to confer the desired degree of sculpturing on the surface 2.

In particular, FIG. 1 concerns the application of microspheres 3 formed from the same material (usually metal) as the stent or from different materials with the subsequent anchorage of the microspheres (the average diameter of which is approximately 10–20 microns) using the method known as "hot partial melting". This is a method known in the art and is used, for example, to confer a surface appearance approximately similar to the surface appearance characteristic of a work-piece obtained by sintering the surfaces of mechanical work-pieces intended for various purposes. From this one understands that such an embodiment can be practiced also in connection with a stent realized, as a whole, or at least in those part(s) corresponding to the surface sculpturing, by sintering.

Figure 2:
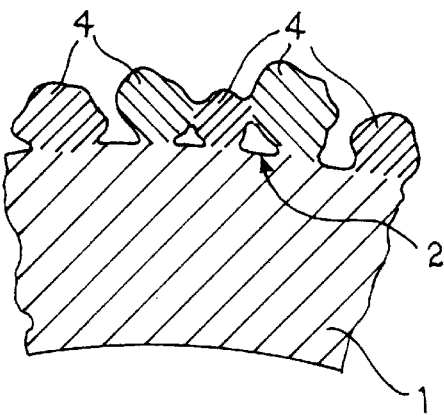

FIG. 2 concerns an embodiment of the arrangement illustrated in FIG. 1 in which, while retaining the same typical surface irregularity, irregular-shape granules 4 are used in place of the microspheres 3. The same remarks made in the foregoing in respect of possibly manufacturing the stent, at least partly, by sintering apply also in this case.

Figure 3:
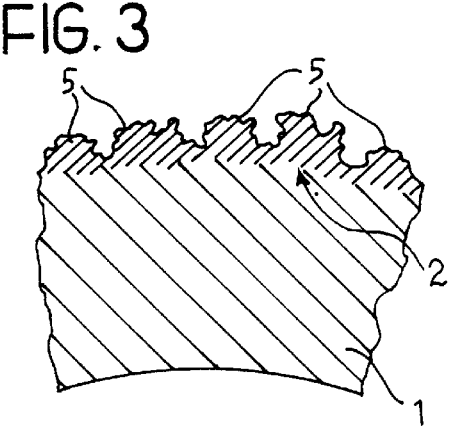

FIG. 3 illustrates a further embodiment based on the deposition of a receptor material using, for example, sputtering or plasma spray techniques to form an irregular-shape accretion 5, for example, having a pseudocolumnar structure.

From this point of view, the solution according to FIG. 1 (the application of microspheres) seems to be preferred when it is desired to create undercuts and roughness on the surface 2, having a mechanical anchorage function and precisely defined geometric characteristics which are identified by the (precisely determinable) grain size of the microspheres 3.

Conversely, the arrangement shown in FIG. 3 appears preferable where the objective is to maximise the effect of increasing the theoretical surface area that is effectively exposed. This latter solution is therefore preferred when, for example, it is desired to apply a coating to the surface of the stent 1, which coating transports and/or is intended to transport active principles and is essentially in the form of a monomolecular layer.

The arrangement according to FIG. 2 constitutes, to a certain extent, a kind of intermediate between the arrangements of FIGS. 1 and 3.

The arrangements to which FIGS. 1 to 3 refer, which comprise possible equivalent arrangements, are characterized by the fact that the surface sculpturing is formed by the application to the surface 2 of material identical with or different from that of the stent 1. These arrangements are generally preferred when greater or smaller undercut zones are desired on the surface 2.

In any case, objects substantially similar to those described at the beginning of this detailed description of the invention can be achieved by treating the surface 2 in ways intended to confer a generally sculpted appearance thereon.

Figure 4:
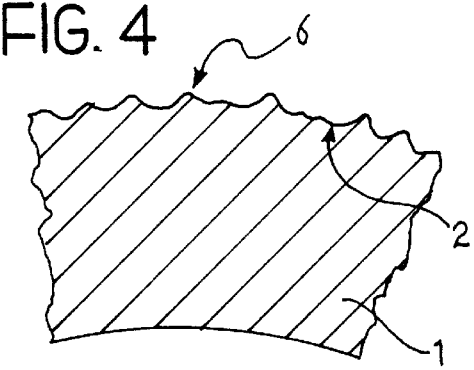

In relation to this, FIG. 4 illustrates the results obtained by subjecting the outer surface 2 to sand-blasting or shot-blasting (a term reserved for a treatment which—instead. of using sand as in sand-blasting is effected using microspheres ("balls") as the ballistic agents, for impact with the treated surface producing roughened surface 6).

Figure 5:
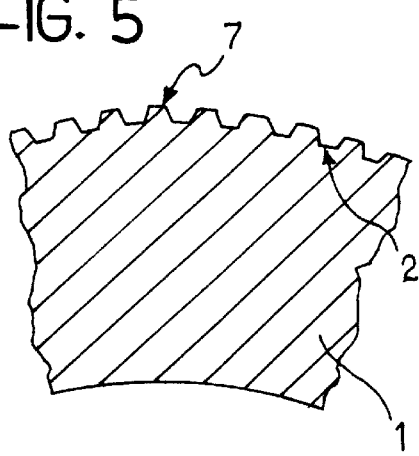

FIG. 5 illustrates the results of a mechanical scoring operation (incision or knurling 7) performed on the outer surface 2 of the stent.

Figure 6:
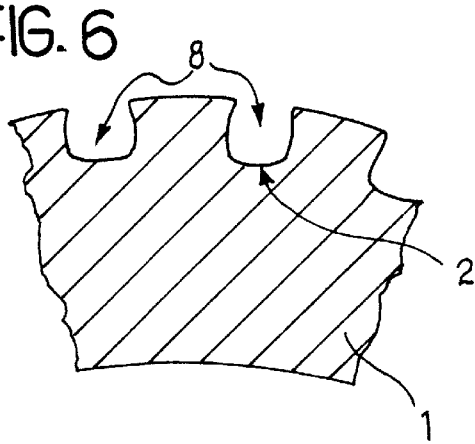

Finally, FIG. 6 illustrates the results obtained from a localized chemical attack (etching) of the surface 2. This method is effected using a resist material (for example, photoresist) which, following exposure through masks or polymerisation using laser beams, is selectively removed from some zones 8 of the surface 2 so as to enable the attack thereof. The resist tracks remaining on the surface 2 are then removed by washing.

This technology is well known in the art (for example, for the manufacture of integrated circuits) and does not need to be illustrated in great detail in this context.

Results substantially similar to those illustrated in FIG. 5 and, in particular, FIG. 6, can also be obtained by incision using laser beams, for example, before or after the operation for cutting the stent structure from a blank constituted by a microtube of metal.

As a rule, all of the solutions illustrated in FIGS. 1 to 6, and any equivalents thereto, can apply to stents. obtained from a metal microtube, possibly manufactured totally or partly by sintering, as well as stents obtained from a wire, the processes illustrated being performed either before or after cutting the tube and/or winding the wire. For reasons of manufacturing simplicity, the applicant has in any case established that it is preferred to form the surface sculpturing before cutting the tube or winding the wire.

What is claimed is:

1. A method of coating a stent with a medication, the stent having a substantially cylindrical shape defined by a stent wall having an interior surface and an exterior surface, the method comprising:

providing a first metal portion;

providing a second metal portion;

sintering the first metal portion to the second metal portion to form at least a portion of the stent wall, the sintering being performed in a manner that causes the exterior surface of the stent wall to be formed with surface irregularities having a surface roughness of 2 to 3 microns; and coating the exterior surface of the stent wall with a medication such that the surface irregularities are substantially coated with the medication.

2. A method of coating a stent with a medication, the stent having a substantially cylindrical shape defined by a stent wall having an interior surface and an exterior surface, the method comprising:

providing a first metal portion;

providing a second metal portion;

sintering the first metal portion to the second metal portion to form at least a portion of the stent wall, the sintering being performed in a manner that causes the exterior surface of the stent wall to be formed with surface irregularities having a pseudocolumnar structure; and coating the exterior surface of the stent wall with a medication such that the surface irregularities are substantially coated with the medication.

3. A method of coating a stent with a medication, the stent having a substantially cylindrical shape defined by a stent wall having an interior surface and an exterior surface, the method comprising:

providing a first metal portion;

providing a second metal portion;

sintering the first metal portion to the second metal portion to form at least a portion of the stent wall, the sintering being performed in a manner that causes the exterior surface of the stent wall to be formed with surface irregularities, the surface irregularities comprising peak-to-trough distances of 10 to 20 microns; and coating the exterior surface of the stent wall with a medication such that the surface irregularities are substantially coated with the medication.

4. A method of coating a stent with a medication, the stent having a substantially cylindrical shape defined by a stent wall having an interior surface and an exterior surface, the method comprising:

providing a first metal portion;

providing a second metal portion;

sintering the first metal portion to the second metal portion to form at least a portion of the stent wall, the sintering being performed in a manner that causes the exterior surface of the stent wall to be formed with surface irregularities; and coating the exterior surface of the stent wall with a medication comprising an antithrombogenic agent such that the surface irregularities are substantially coated with the medication.

5. A method of coating a stent with a medication, the stent having a substantially cylindrical shape defined by a stent wall having an interior surface and an exterior surface, the method comprising:

providing a first metal portion;

providing a second metal portion;

sintering the first metal portion to the second metal portion to form at least a portion of the stent wall, the sintering being performed in a manner that causes the exterior surface of the stent wall to be formed with surface irregularities; and coating the exterior surface of the stent wall with a medication comprising an agent that resists tissue proliferation such that the surface irregularities are substantially coated with the medication.

6. A method of forming a stent to increase the amount of medication with which the stent can be coated, the stent including a substantially cylindrical body portion having a surface area including an interior surface and an exterior surface, the method comprising:

sand-blasting at least one of the interior and exterior surfaces of the body portion to increase the surface area of the body portion.

7. A method of forming a stent to increase the amount of medication with which the stent can be coated, the stent including a substantially cylindrical body portion having a surface area including an interior surface and an exterior surface, the method comprising:

mechanically scoring at least one of the interior and exterior surfaces of the body portion to increase the surface area of the body portion.

\* \* \* \* \*